(12) United States Patent
Iwata

(10) Patent No.: US 7,347,936 B2
(45) Date of Patent: Mar. 25, 2008

(54) LIQUID CHROMATOGRAPH

(75) Inventor: Yosuke Iwata, Kyoto (JP)

(73) Assignees: Shimadzu Corporation, Kyoto-shi (JP); Eisai R&D Management Co., Ltd., Tokyo (JP)

( * ) Notice: Subject to any disclaimer, the term of this patent is extended or adjusted under 35 U.S.C. 154(b) by 280 days.

(21) Appl. No.: 11/034,638

(22) Filed: Jan. 13, 2005

(65) Prior Publication Data

US 2005/0167348 A1 Aug. 4, 2005

(30) Foreign Application Priority Data

Jan. 30, 2004 (JP) ............................. 2004-024765

(51) Int. Cl.
*B01D 15/08* (2006.01)
(52) U.S. Cl. ................... 210/198.2; 210/656; 210/659; 422/70
(58) Field of Classification Search ............. 210/198.2, 210/656, 659, 101; 422/70
See application file for complete search history.

(56) References Cited

U.S. PATENT DOCUMENTS

| | | | | |
|---|---|---|---|---|
| 5,117,109 A | * | 5/1992 | Asakawa et al. ........... 250/288 |
| 5,372,716 A | * | 12/1994 | Levy et al. ............... 210/198.2 |
| 5,458,783 A | * | 10/1995 | Levy et al. ................. 210/659 |
| 6,780,325 B1 | * | 8/2004 | Murata et al. .............. 210/656 |
| 6,802,967 B2 | * | 10/2004 | Masuda et al. .......... 210/198.2 |
| 6,942,793 B2 | * | 9/2005 | Ito et al. .................. 210/198.2 |
| 2003/0168392 A1 | * | 9/2003 | Masuda et al. .......... 210/198.2 |
| 2005/0218055 A1 | * | 10/2005 | Hayashi et al. .......... 210/198.2 |

FOREIGN PATENT DOCUMENTS

JP 2002-372522 12/2002

OTHER PUBLICATIONS

Machine Translation of Japan Patent No. 2002-372522, pp. 1-7.*

* cited by examiner

*Primary Examiner*—Ernest G. Therkorn
(74) *Attorney, Agent, or Firm*—Rankin, Hill & Clark LLP

(57) ABSTRACT

A liquid chromatograph has switching valves as a flow passage switching mechanism and an automatic sampler as an injection section. The liquid chromatograph can switch, by switching the switching valves between a concentration flow passage for concentrating the sample injected by the automatic sample via a flow passage which connects the automatic sampler to the trapping column; a concentration analysis flow passage for separating and analyzing the concentrated sample on a per-composition basis which connects the trapping column to the analysis column; and a direct analysis flow passage by separating the sample on a per-composition basis which connects the automatic sampler to the analysis column.

3 Claims, 5 Drawing Sheets

LIQUID CHROMATOGRAPH

BACKGROUND OF THE INVENTION

1. Field of the Invention

The present invention relates to a liquid chromatograph having a trapping column for analyzing a dilute sample through concentration.

2. Description of the Related Art

In relation to a high-performance liquid chromatograph, when a sample is injected into an injection port, the thus-injected sample is usually sent to an analysis column by means of a mobile phase sent by a liquid delivery pump, and the sample is separated by the analysis column. When the sample injected into the injection port is of large quantity, a band of the sample in the analysis column is broadened by action of a solvent contained in the sample, so that the separation performance of the analysis column is reduced, thereby posing difficulty in highly-sensitive analysis. However, in the analysis of a diluted sample, a large quantity of sample must be injected in order to increase the absolute quantity of sample during analysis. In such a case, analysis is usually carried out by means of online concentration using a trapping column.

FIG. 5 is a flow passage diagram showing an example liquid chromatograph, wherein FIG. 5A shows an online concentration flow passage, and FIG. 5B shows a direct analysis flow passage.

As shown in FIG. 5A, in analysis involving concentration of a sample, a mobile phase solvent 5 is sent by a pump 10, thereby eluting the sample injected into the flow passage by an automatic sampler 18, and the thus-eluted sample is sent to a trapping column 20 via a switching valve 16. The sample is trapped in the trapping column 20, whereupon the sample is concentrated. After concentration of the sample, mobile phases 2a, 2b for analysis purpose are sent to a mixer 22 by analysis pumps 8a, 8b. The composition of the mobile phase is adjusted by controlling the flow rate of each of the analysis pumps 8a, 8b, to thus enable a gradient analysis. The mobile-phase solution mixed by the mixer 22 is sent to the trapping column 20 via the valve 16, thereby eluting the sample trapped by said trapping column 20 and sending the eluted sample to an analysis column 24. The sample is separated on a per-composition basis by the analysis column 24, and the thus-separated sample is detected by a detector 26.

In the direct analysis not involving concentration, the sample is injected to a position downstream of the mixer 22 directly from the automatic sampler 18, as shown in FIG. 5B. The sample injected into the flow passage is sent to the analysis column 24, where the sample is separated on a per-composition basis. The thus-separated compositions are detected by the detector 26.

In order to examine the concentration efficiency of the trapping column and deterioration of the column by means of online concentration analysis using the trapping column, identical samples were subjected to analysis using the online trapping column and analysis using the ordinary analysis column, and the results were compared with each other, to thus measure a recovery rate. In order to measure the recovery rate, the related-art liquid chromatograph was subjected to a change from (A) the online concentration flow passage to (B) the direct analysis flow passage. Operation for changing the plumbing is very complicated, and involves consumption of much time and consideration for prevention of leakage which would otherwise arise after changing of the plumbing; particularly, a dead volume in the plumbing for which micro flow rate or nano flow rate is critical.

SUMMARY OF THE INVENTION

An object of the present invention is to provide a liquid chromatograph capable of switching between online concentration analysis and direct analysis not involving concentration, without a change in plumbing.

A liquid chromatograph of the present invention comprises:

an injection section for injecting a sample into a flow passage;

an analysis column for separating the injected sample on a per-composition basis;

a detector for detecting compositions of the sample separated by the analysis column;

a trapping column for concentrating the sample; and a flow passage switching mechanism for switching between a concentration flow passage connecting the injection section to the trapping column, a concentration analysis flow passage connecting the trapping column to the analysis column, and a direct analysis flow passage connecting the injection section to the analysis column, such that one or two of the concentration flow passage, the concentration analysis flow passage, and the direct analysis flow passage are activated.

Moreover, the liquid chromatograph may comprise two trapping columns, and the flow passage switching mechanism may simultaneously activate the concentration flow passage and the concentration analysis flow passage through the trapping columns.

Since the liquid chromatograph is provided with the flow passage switching mechanism capable of switching a flow passage between the direct analysis flow passage and the concentration analysis flow passage, complicated changes in plumbing can be omitted.

Further, either the direct analysis flow passage or the analysis flow passage not involving concentration can be selected by means of the concentration of the sample as well as by measurement of the recovery rate. Hence, samples ranging from a diluted sample to a high-concentration sample can be analyzed by a single analyzer.

DETAILED DESCRIPTION OF THE INVENTION

First Embodiment

Figure 1:
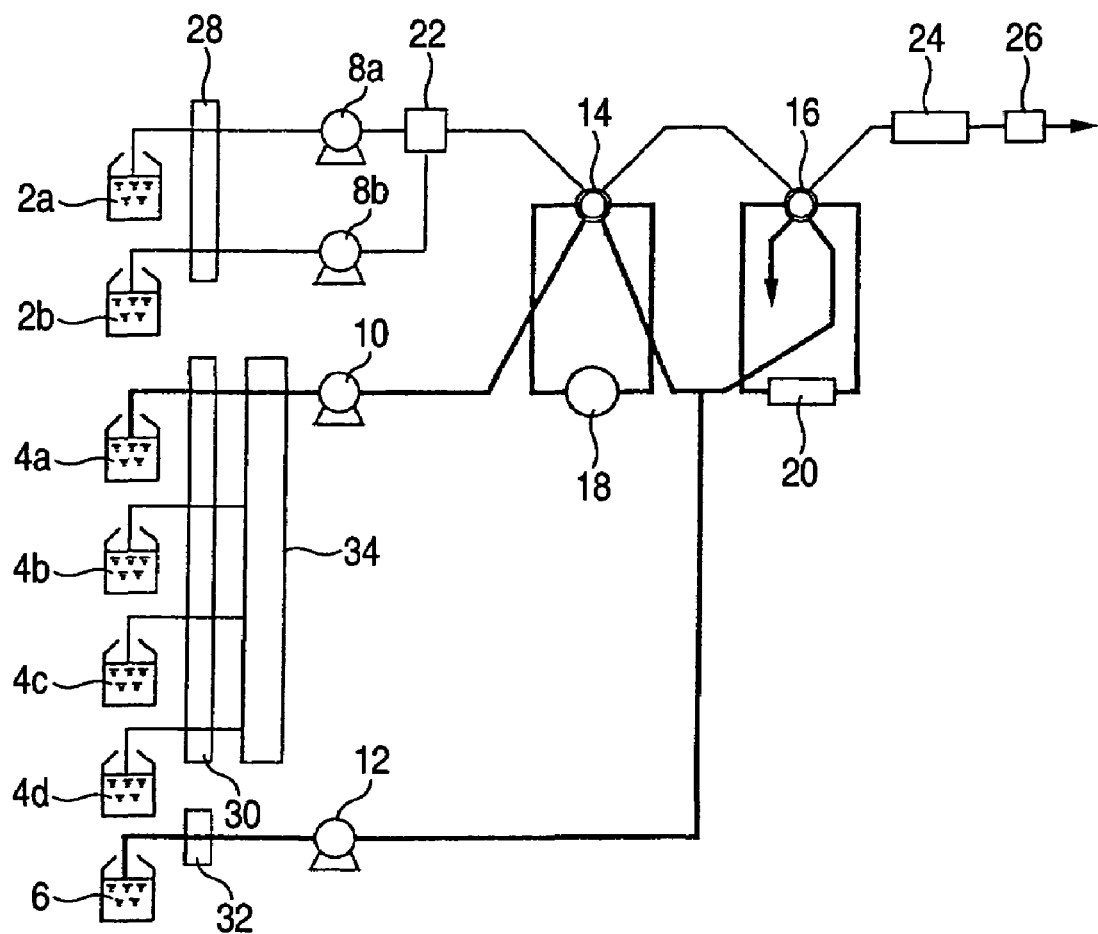
FIG. 1 is a flow passage diagram schematically showing the configuration of a liquid chromatograph according to an embodiment of the invention, showing the phase of concentration of a sample.
Figure 2:
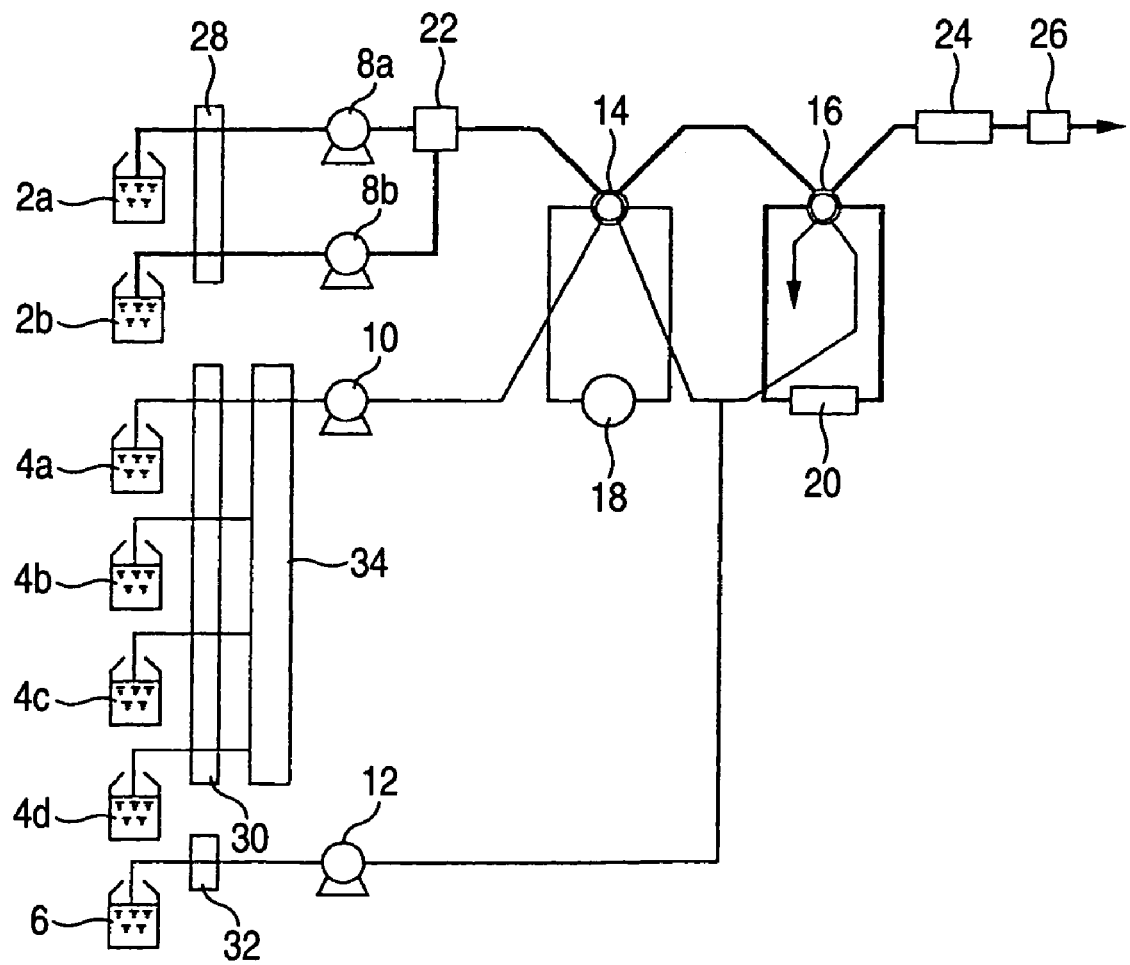
FIG. 2 is a flow passage diagram schematically showing the configuration of the liquid chromatograph according to the embodiment, showing analysis performed after concentration of the sample.
Figure 3:
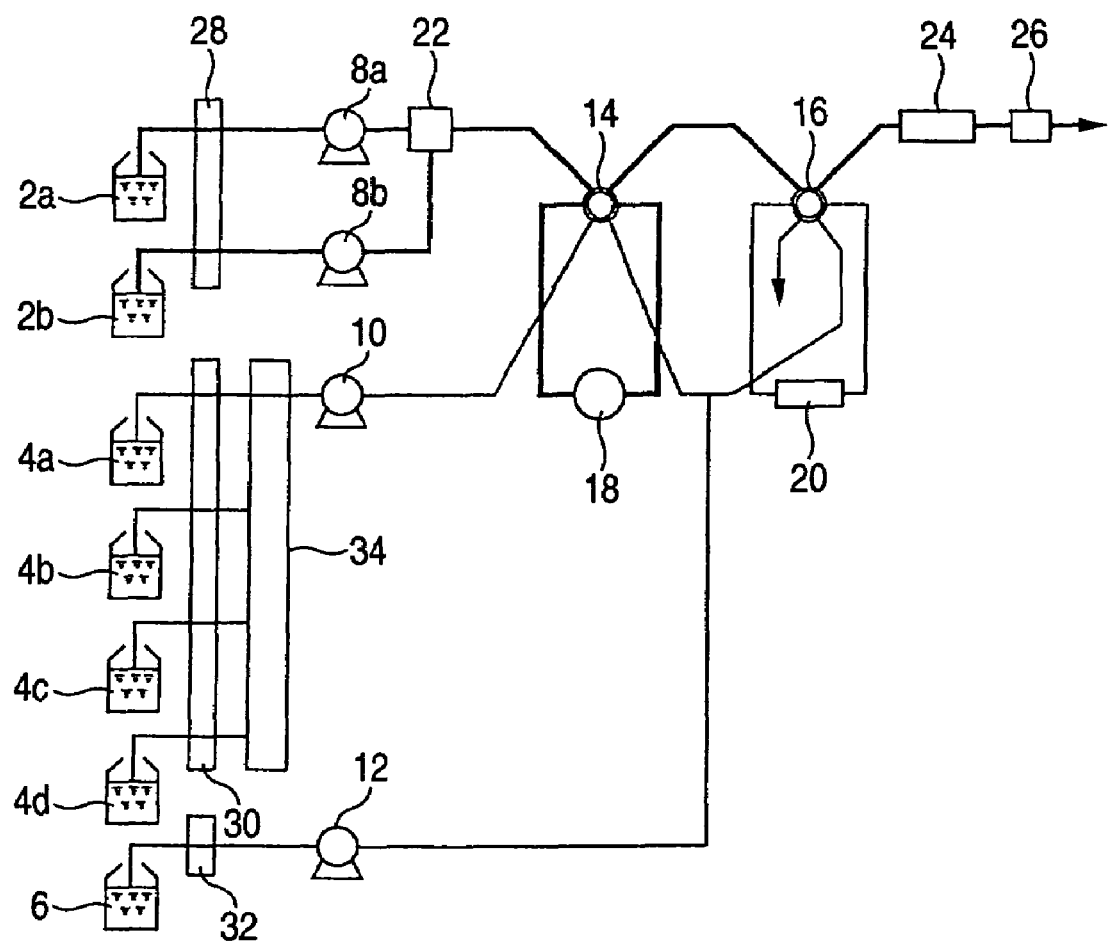
FIG. 3 is a flow passage diagram schematically showing the configuration of the liquid chromatograph according to the embodiment, showing the phase of direct analysis.

An embodiment will be provided below. FIGS. 1, 2, and 3 are flow passage diagrams showing an embodiment of a liquid chromatograph according to the present invention. FIG. 1 shows a flow passage achieved at the phase of concentration of a sample, FIG. 2 shows a flow passage achieved at the phase of concentration analysis, and FIG. 3 shows a flow passage achieved at the phase of direct analysis.

The liquid chromatograph has switching valves 14, 16 as a flow passage switching mechanism, and an automatic sampler 18 as an injection section. The liquid chromatograph can switch, by switching the switching valves 14, 16, between a concentration flow passage for concentrating the sample injected by the automatic sampler 18; a concentration analysis flow passage for separating the trapped sample on a per-composition basis; and a direct analysis flow passage for separating the sample on a per-composition basis. The concentration flow passage connects the automatic sampler 18 to a trapping column 20. The concentration analysis flow passage connects the trapping column 20 to the analysis column 24. The direct analysis flow passage connects the automatic sampler 18 to the analysis column 24.

Reference numerals 2a, 2b denote analysis mobile phases used for sending a sample to the analysis column 24, and analysis pumps 8a, 8b are provided for sending the analysis mobile phases. Gradient analysis can be performed by means of adjustment of composition of the mobile phases by controlling the flow rate of the analysis pump 8a and that of the analysis pump 8b. A mixer 22 is disposed downstream of the analysis pumps 8a, 8b for mixing the analysis mobile phases 2a, 2b.

Reference numerals 4a, 4b, 4c, and 4d denote mobile phases for sending a sample to the trapping column, and a sample delivery pump 10 is provided for sending the mobile phases.

Reference numeral 6 denotes a dilution fluid, the dilution fluid 6 is sent by a dilution pump 12 via a flow passage, and the flow passage merges with a flow passage between the switching valve 14 and the switching valve 16.

A mobile-phase switching valve 34 is provided upstream of the pump 10, thereby enabling selective sending of any one of the mobile phases 4a, 4b, 4c, and 4d. Degassers 28, 30, and 32 are provided upstream of the pumps 8a, 8b, 10, and 12, thereby removing bubbles contained in the mobile phases and the diluted fluid.

The sample having been separated on a per-composition basis by the analysis column 24 is sent to and detected by a downstream detector 26.

Operation of the embodiment will now be described.

[Concentration]

In FIG. 1, a flow passage shown by thick lines denotes a concentration flow passage through which the liquid phases and the sample flow at the phase of concentration of the sample. Any one is selected from mobile phases 4a, 4b, 4c, and 4d by means of the mobile phase switching valve 34, and the thus-selected mobile phase is sent from the pump 10 to the automatic sampler 18 via the switching valve 14. The automatic sampler 18 aspirates a sample from a sample vial (omitted from the drawing), and the thus-aspirated sample is sent to the trapping column 20 via the switching valve 16 along with the sample delivery mobile phase. At this time, the dilution fluid 6 is sent from the pump 12 and merges with the mobile phase sent from the automatic sampler 18 at the flow passage located between the switching valve 14 and the switching valve 16. The mobile phase containing the sample is sent to the trapping column 20 while being diluted with the dilution fluid 6. In the trapping column 20, the sample is concentrated as a result of the composition of the sample being trapped. The mobile phase having passed by the trapping column 20 and the solution of the dilution fluid are discharged to a drain via the switching valve 16.

Analysis after Concentration

In FIG. 2, a flow passage indicated by thick lines is a concentration analysis flow passage through which the analysis mobile phase and the sample flow when the trapped sample is sent to the analysis column 24, wherein the switching valve 16 has been switched from the state shown in FIG. 1. The mobile phase solution delivered from the mixer 22 is sent to the switching valve 16 via the switching valve 14 and sent to the trapping column 20. The sample trapped by the trapping column 20 is diluted with the sent mobile-phase solution. The thus-diluted sample is sent to the analysis column 24 via the switching valve 16 along with the mobile phase and is separated on a per-composition basis, and the thus-separated compositions are detected by the detector 26.

[Ordinary Analysis]

In FIG. 3, in the case of direct analysis where a sample is separated and analyzed without involvement of concentration, the switching valves 14, 16 are switched such that the sample migrates through the direct analysis flow passage indicated by the thick line along with the mobile phase. The direct analysis obviates a necessity for sending the mobile phases 4a, 4b, 4c, and 4d for transporting a sample and the dilution fluid 6. The sample aspirated by the automatic sampler 18 is sent to the analysis column 24 via the switching valves 14 to 16 along with the sent mobile-phase solution. After having been separated, the sample is detected by the detector 26.

Second Embodiment

Figure 4:
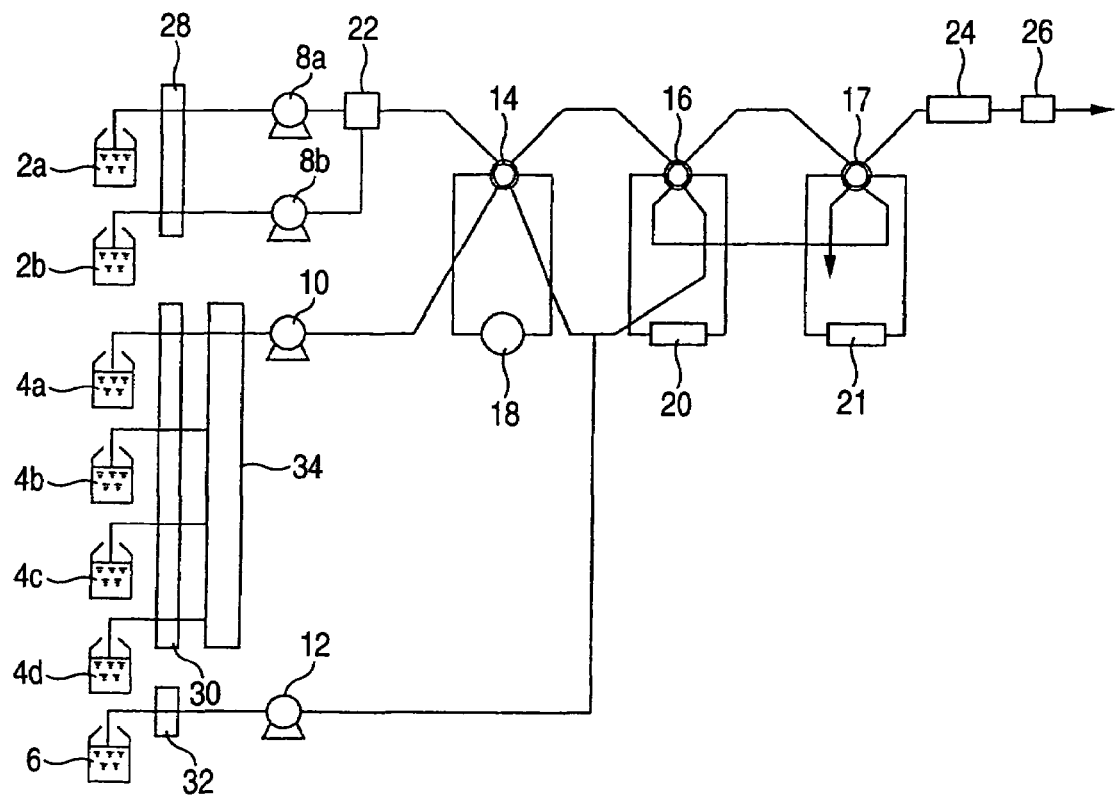
FIG. 4 is a flow passage diagram showing the configuration of an embodiment of a liquid chromatograph having two trapping columns.
Figure 5A:
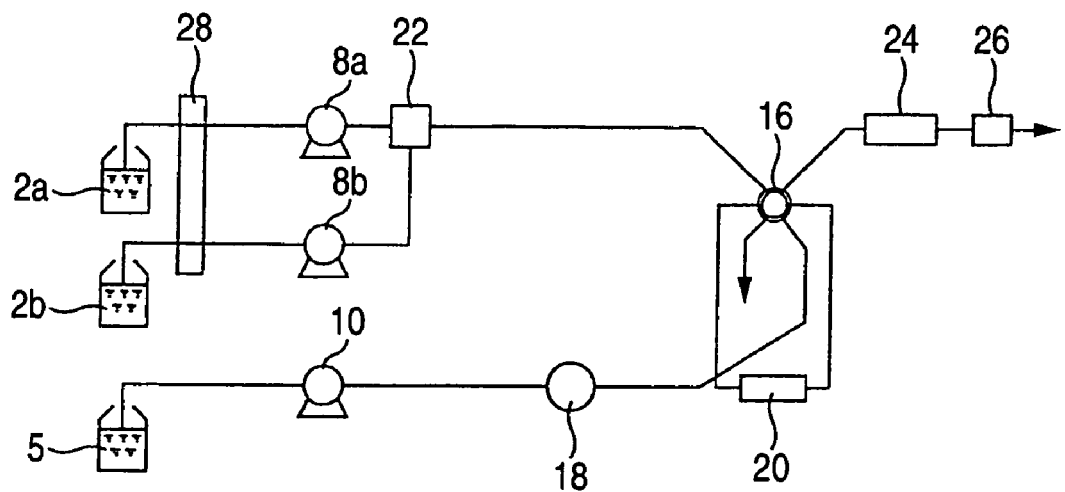
FIGS. 5A and 5B are flow passage diagrams schematically showing the configuration of a common liquid chromatograph.
Figure 5B:
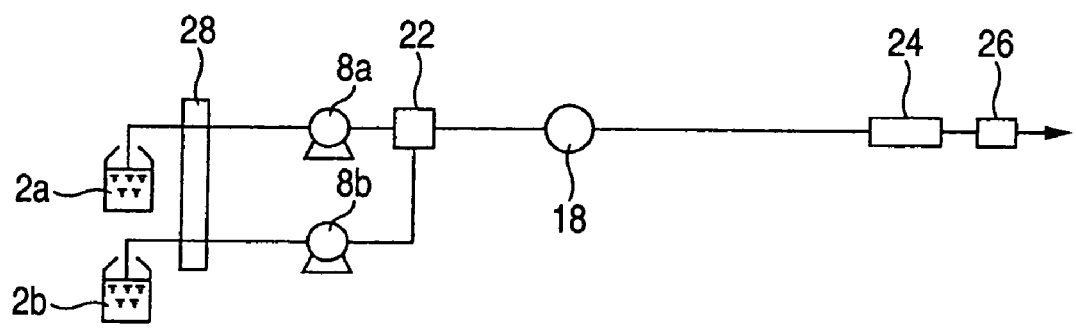

There will be described hereinbelow a second embodiment where a second trapping column is provided in the flow passage of the liquid chromatograph described in connection with the first embodiment. FIG. 4 is a flow passage diagram showing the configuration of a liquid chromatograph having two trapping columns.

A switching valve 17 and a second trapping column 21 are provided downstream of the switching valve 16 and the trapping column 20 shown in FIGS. 1 through 3. This apparatus is configured to simultaneously enable concentration of a sample and analysis of the concentrated sample.

Operation of the liquid chromatograph of the present embodiment will be described hereinbelow.

Concentration of the sample is performed as follows. Namely, the mobile phase switching valve 34 selects any one from the mobile phases 4a, 4b, 4c, and 4d and sends the thus-selected mobile phase to the automatic sampler 18 by the pump 10. The automatic sampler 18 aspirates a sample from the sample vial or the like (omitted from the drawing), and the thus-aspirated sample is sent to the trapping column 20 via the switching valve 16 along with the sample delivery mobile phase or sent to the trapping column 21 via the switching valves 16, 17. At this time, the dilution fluid 6 is sent from the pump 12 and merges with the sample at the flow passage located between the switching valves 14 and 16. The mobile phase is sent to the trapping column 20 or the trapping column 21 while being diluted. The sample is concentrated in the trapping column 20 or 21 as a result of compositions of the sample being trapped.

By means of switching the switching valves 16, 17, this apparatus can concentrate the sample by alternately using the trapping column 20 and the trapping column 21. For instance, during a period in which the sample is being concentrated in the trapping column 20, compositions of the sample trapped by the trapping column 21 are diluted with the mobile-phase solution sent from the mixer 22 and sent to the analysis column 24. Thus, alternate use of the two trapping columns enables analysis even during the course of concentration of the sample.

Moreover, when concentration is not performed, the mobile phase can be sent directly to the analysis column 24 via the automatic sampler 18 and without passing through the trapping columns 20, 21, by switching the switching valves 14, 16, and 17.

As mentioned above, the trapping columns are connected to each other via the switching valves. The switching valves can be switched between a case where the trapping columns are connected to the flow passage and a case where the trapping column is not connected to the flow passage. Hence, there is no necessity for rearranging plumbing between a case where concentration is performed and a case where concentration is not performed.

Further, as a result of provision of two trapping columns, another sample can be analyzed during the course of concentration of the sample. Hence, the operating efficiency of the apparatus can be enhanced.

What is claimed is:

1. A liquid chromatograph comprising:
   an injection section for injecting a sample into a flow passage;
   an analysis column for separating said injected sample on a per-composition basis;
   a detector for detecting compositions of the sample separated by said analysis column;
   a trapping column for concentrating said sample; and
   a flow passage switching mechanism containing at least a first and second connected multi-port valve, said first multi-port valve having two ports for connecting to said injector section, said second multi-port valve having two ports for connection to said trapping column, said flow passage switching mechanism allowing switching between a concentration flow passage connecting said injection section to said trapping column, a concentration analysis flow passage connecting said trapping column to said analysis column, and a direct analysis flow passage connecting said injection section to said analysis column, such that one or two of said concentration flow passage, said concentration analysis flow passage, and said direct analysis flow passage are activated.

2. The liquid chromatograph according to claim 1, wherein said liquid chromatograph comprises two or more trapping columns, and said flow passage switching mechanism simultaneously activates said concentration flow passage and said concentration analysis flow passage through said trapping columns.

3. The liquid chromatograph according to claim 1, wherein said flow passage switching mechanism includes first and second switching valves, and wherein the injection section and the first switching valve are connected via a first passage, the first switching valve and the trapping column are connected via a second passage, the trapping column and the second switching valve are connected via a third passage, the second switching valve and the analysis column are connected via a forth passage, and the first and second switching valves are connected via a fifth passage, and wherein the first and second passages constitute the concentration flow passage, the third and fourth passages constitute the concentration analysis flow passage, and the first, fourth and fifth passages constitute the direct analysis flow passage.

* * * * *